(12) United States Patent
Zeijlemaker

(10) Patent No.: US 8,260,418 B2
(45) Date of Patent: Sep. 4, 2012

(54) SYSTEM FOR WAVEFORM STIMULATION COMPENSATING ELECTRODE POLARIZATION

(75) Inventor: Volkert A. Zeijlemaker, Landgraaf (NL)

(73) Assignee: Medtronic, Inc., Minneapolis, MN (US)

(*) Notice: Subject to any disclaimer, the term of this patent is extended or adjusted under 35 U.S.C. 154(b) by 416 days.

(21) Appl. No.: 12/536,786

(22) Filed: Aug. 6, 2009

(65) Prior Publication Data

US 2010/0016912 A1 Jan. 21, 2010

Related U.S. Application Data

(62) Division of application No. 11/096,943, filed on Mar. 31, 2005, now Pat. No. 7,577,480.

(51) Int. Cl.
*A61N 1/362* (2006.01)
(52) U.S. Cl. ......................................................... 607/11
(58) Field of Classification Search ................... 607/7, 9, 607/11, 13–14, 72
See application file for complete search history.

(56) References Cited

U.S. PATENT DOCUMENTS

| 4,316,472 | A | | 2/1982 | Mirowski et al. |
|---|---|---|---|---|
| 4,343,312 | A | * | 8/1982 | Cals et al. .................. 607/13 |
| 4,373,531 | A | * | 2/1983 | Wittkampf et al. .......... 607/13 |
| 4,375,817 | A | | 3/1983 | Engle et al. |
| 4,379,459 | A | | 4/1983 | Stein |
| 4,384,585 | A | | 5/1983 | Zipes |
| 4,476,868 | A | | 10/1984 | Thompson |
| 455,606 | A | | 12/1985 | Thompson et al. |
| 4,577,633 | A | | 3/1986 | Berkovits et al. |
| 4,587,970 | A | | 5/1986 | Holley et al. |
| 4,726,380 | A | | 2/1988 | Vollmann et al. |
| 4,727,877 | A | | 3/1988 | Kallok |
| 4,800,883 | A | | 1/1989 | Winstrom |
| 4,821,723 | A | | 4/1989 | Baker, Jr. et al. |
| 4,830,006 | A | | 5/1989 | Haluska et al. |

(Continued)

FOREIGN PATENT DOCUMENTS

EP 0605244 6/1994

(Continued)

OTHER PUBLICATIONS

Olson, et al., "Onset and Stability for Ventricular Tachyarrhythmia Detection in an Implantable Pacer-Cardioverter-Defibrillator", Computers in Cardiology, Oct. 7-10, 1986, pp. 167-170, IEEE Computer Science Press.

(Continued)

*Primary Examiner* — Carl H Layno
*Assistant Examiner* — Roland Dinga
(74) *Attorney, Agent, or Firm* — Reed A. Duthler

(57) ABSTRACT

Upon delivery of a pacing pulse to a heart by an electrode of an implantable medical device (IMD), a deleterious pace polarization artifact is generally created at the electrode-tissue interface and subsequently stored by the electrode. Such polarization artifact is generally minimized through the use of passive recharge circuitry. Such passive recharge circuitry functions in creating a recharge pulse at the electrode which in essence, minimizes the polarization artifact on the electrode. In order to produce further artifact minimization from a subsequent pacing pulse, following termination of the recharge pulse, any remaining polarization artifact is sampled and analyzed by the IMD and IMD software optionally compensates the next recharge pulse to further minimize the polarization artifact generated by a next pacing pulse. This sampling and optional compensation is repeated for subsequent pacing pulses so that polarization artifacts are effectively analyzed and if necessary, minimized.

4 Claims, 10 Drawing Sheets

U.S. PATENT DOCUMENTS

| | | | |
|---|---|---|---|
| 4,880,005 A | 11/1989 | Pless et al. | |
| 4,928,688 A | 5/1990 | Mower | |
| 4,949,719 A | 8/1990 | Pless et al. | |
| 4,953,551 A | 9/1990 | Mehra et al. | |
| 4,955,376 A | 9/1990 | Callaghan et al. | |
| 4,969,460 A | 11/1990 | Callaghan et al. | |
| 4,969,461 A | 11/1990 | Callaghan et al. | |
| 4,969,462 A | 11/1990 | Callaghan et al. | |
| 4,969,464 A | 11/1990 | Callaghan et al. | |
| 4,969,467 A | 11/1990 | Callaghan et al. | |
| 5,099,838 A | 3/1992 | Bardy | |
| 5,117,824 A | 6/1992 | Keimel et al. | |
| 5,131,388 A | 7/1992 | Pless et al. | |
| 5,144,949 A | 9/1992 | Olson | |
| 5,158,078 A | 10/1992 | Bennett et al. | |
| 5,163,427 A | 11/1992 | Keimel | |
| 5,172,690 A * | 12/1992 | Nappholz et al. | 607/13 |
| 5,184,615 A | 2/1993 | Nappholz et al. | |
| 5,188,105 A | 2/1993 | Keimel | |
| 5,269,298 A | 12/1993 | Adams et al. | |
| 5,312,453 A | 5/1994 | Shelton et al. | |
| 5,314,430 A | 5/1994 | Bardy | |
| 5,324,310 A | 6/1994 | Greeninger et al. | |
| 5,354,316 A | 10/1994 | Keimel | |
| 5,417,718 A | 5/1995 | Kleks et al. | |
| 5,545,186 A | 8/1996 | Olson et al. | |
| 5,609,611 A * | 3/1997 | Bolz et al. | 607/13 |
| 5,690,683 A | 11/1997 | Haefner et al. | |
| 5,690,686 A | 11/1997 | Min et al. | |
| 5,741,312 A | 4/1998 | Vonk et al. | |
| 5,792,203 A | 8/1998 | Schroeppel | |
| 5,800,465 A | 9/1998 | Thompson et al. | |
| 5,861,013 A | 1/1999 | Peck et al. | |
| 5,893,882 A | 4/1999 | Peterson et al. | |
| 5,954,756 A | 9/1999 | Hemming et al. | |
| 5,964,787 A | 10/1999 | Kerver et al. | |
| 6,067,472 A * | 5/2000 | Vonk et al. | 607/28 |
| 6,081,748 A | 6/2000 | Struble et al. | |
| 7,089,049 B2 | 8/2006 | Kerver et al. | |
| 7,363,078 B2 | 4/2008 | Vonk et al. | |
| 2002/0183798 A1 | 12/2002 | Vonk | |
| 2003/0083697 A1 | 5/2003 | Baudino et al. | |
| 2004/0215274 A1 | 10/2004 | Kerver et al. | |
| 2004/0215275 A1* | 10/2004 | Vonk et al. | 607/28 |
| 2004/0230242 A1* | 11/2004 | van Dam et al. | 607/27 |

FOREIGN PATENT DOCUMENTS

| | | |
|---|---|---|
| EP | 0748637 | 12/1996 |
| WO | WO 92/18198 | 10/1992 |
| WO | WO 98/48894 | 11/1998 |
| WO | WO 2004/096036 | 11/2004 |
| WO | WO 2004/096357 | 11/2004 |

OTHER PUBLICATIONS

Arzbaecher, et al., "Automatic Tachycardia Recognition", PACE, May-Jun. 1984, pp. 541-547.

* cited by examiner

SYSTEM FOR WAVEFORM STIMULATION COMPENSATING ELECTRODE POLARIZATION

CROSS-REFERENCE TO RELATED APPLICATIONS

This application is a divisional of U.S. patent application Ser. No. 11/096,943 filed on Mar. 31, 2005 which is now U.S. Pat. No. 7,577,480. The disclosure of the above application is incorporated herein by reference.

FIELD OF THE INVENTION

The invention relates generally to the field of implantable medical devices, and more particularly, to therapy delivery devices.

BACKGROUND OF THE INVENTION

A wide variety of implantable therapy delivery devices have been developed including pacemakers, cardioverter/defibrillators, and cardiomyostimulators. For many individuals with heart disease, these devices provide the best and sometimes the only therapy to restore the individuals to a more healthful condition and a fuller life.

Pacemakers, for example, are typically designed to operate using various different response methodologies, such as, for example, nonsynchronous or asynchronous (fixed rate), inhibited (stimulus generated in the absence of a specified cardiac activity), or triggered (stimulus delivered in response to a specific hemodynamic parameter). Generally, inhibited and triggered pacemakers may be grouped as "demand"-type pacemakers, in which a pacing pulse is only generated when demanded by the heart. To determine when pacing is required by the pacemaker, demand pacemakers may sense various conditions such as heart rate, physical exertion, temperature, and the like. Moreover, pacemaker implementations range from the simple fixed rate, single chamber device that provides pacing with no sensing function, to highly complex models that provide fully-automatic dual chamber pacing and sensing functions. For example, such multiple chamber pacemakers are described in U.S. Pat. No. 4,928,688 to Mower entitled "Method and Apparatus for Treating Hemodynamic Dysfunction," issued May 29, 1990; U.S. Pat. No. 5,792,203 to Schroeppel entitled "Universal Programmable Cardiac Stimulation Device," issued Aug. 11, 1998; U.S. Pat. No. 5,893,882 to Peterson et al. entitled "Method and Apparatus for Diagnosis and Treatment of Arrhythmias," issued Apr. 13, 1999; and U.S. Pat. No. 6,081,748 to Struble et al. entitled "Multiple Channel, Sequential Cardiac Pacing Systems," issued Jun. 27, 2000.

Pacemakers include cardiac lead electrodes for delivering cardiac therapy. Generally, such electrodes are used to stimulate cardiac tissue with electrical impulses having amplitudes ranging in volts, e.g., from about 1 volt to about 10 volts. Most "demand"-type pacemakers also include sense amplifier circuitry. Such circuitry generally includes sense amplifiers for recording and/or deriving sensed cardiac electrical activity. Generally, such amplifiers are low current, low voltage devices and are used to sense heart cardiac signals typically having amplitudes ranging in millivolts, e.g., from about 1 millivolt to about 20 millivolts. The sense amplifiers are used to control the delivery of therapy in accordance with a pre-defined algorithm. As such, pacemakers may be (i) prompted to generate electrical stimulating pulses if a heart needs therapy or (ii) inhibited from generating unnecessary output electrical stimulating pulses if a heart is functioning properly. Dual-chamber cardiac pacemakers, for example, typically have separate sense amplifiers for atrial and ventricular sensing. The sense amplifiers detect the presence of intrinsic signals, such as P-waves occurring naturally in the atrium and R-waves occurring naturally in the ventricle. As mentioned, upon detecting intrinsic signals from the heart, the sense amplifier circuitry generates a digital signal (for output to other components), which can either prompt or inhibit the delivery of a pacing pulse to the corresponding chamber via the electrodes.

In the case where a pacing pulse is delivered to cardiac tissue, immediately following such delivery, a residual pace polarization artifact (also called a post-pace polarization artifact or a pace polarization signal) is typically generated. Such an artifact is generally some fraction of the pacing pulse. With respect to impedance sensed by the device's internal circuitry, the total load of the pacing circuit comprises the impedance of the lead itself, the electrode-tissue interface impedances, and the impedance of the body tissue bulk. The impedances of the body tissue and the lead may be modeled as a simple series bulk resistance, leaving the electrode-tissue interface as the capacitive energy absorbing/discharging element of the total load. As such, the artifact generated by the pacing pulse is temporarily captured at the interface between pacing electrode and cardiac tissue. Subsequently, the energy of the pace polarization artifact discharges, creating an after-potential. Generally, the tip and ring electrodes serve as storage elements for the after-potential; however, the tip electrode is the primary after-potential storage element in comparison to the ring electrode.

Subsequently, if the pacing pulse captures the heart and causes an evoked response in the cardiac tissue, the evoked response signal is superimposed atop the typically much larger amplitude pace polarization artifact. As a result, conventional pacemakers or pacemaker-cardioverter/defibrillators ("PCD's") either cannot differentiate, or have difficulty differentiating, between pace polarization artifacts and evoked response signals. This problem is further complicated by the fact that residual pace polarization artifacts typically have high amplitudes even when evoked response signals do occur. Consequently, it becomes difficult, if not impossible, to detect an evoked response signal using a conventional pacemaker or PCD sense amplifier employing linear frequency filtering techniques. As a result, many pacemakers cannot effectively discern between pace polarization artifacts and evoked response signals.

Pacemakers have been employed to use sensing and timing circuits that do not attempt to detect evoked response signals until the pace polarization artifact is no longer present or has subsided to some minimal amplitude level; only then is sensing considered reliable. This is generally due to the limited dynamic range of the sensing amplifiers. With respect to capture detection, in which the pacemaker detects whether the pacing pulse to the cardiac tissue evoked an effective stimulated response, such sensing typically occurs a significant period of time after the evoked response signal has already occurred. As a result, such pacemakers may not accurately detect evoked response signals.

Pacemakers have also been employed to minimize the pace polarization artifacts by maintaining some sort of charge balance. These designs typically involve using passive charge circuitry (e.g., analog circuitry) to minimize the artifact from the electrode. However, even by minimizing the pace polarization artifact in this fashion, an artifact may still remain that is beyond the millivolt dynamic range of the sense amplifier so as to make the evoked response difficult to differentiate.

Further, the charge balance using such circuitry is often gradually achieved (e.g., in hundreds of milliseconds), increasing the likelihood that the evoked response, which can occur quickly after the stimulus signal during tachycardia or fibrillation episodes (e.g., within 5 to 20 milliseconds after the stimulus signal), may be missed.

In summary, when providing cardiac therapy using implantable therapy delivery devices, the generation and delivery of an electrical pulse to the heart gives rise to charge in the electrode-tissue interface. Such charge leads to the creation of pace polarization artifacts, which typically have much larger amplitudes than those corresponding to electrical signals arising from an intrinsic heartbeat or a stimulated response. In turn, the pace polarization artifacts can interfere with the detection and analysis of an evoked response to a pacing pulse. Methods have been developed to address this problem, all of which generally have shortcomings. Thus, a need exists in the medical arts for a system, which reliably senses evoked response signals in a pacing environment so as to overcome the problems mentioned above, among others.

BRIEF SUMMARY OF THE INVENTION

Upon delivery of a pacing pulse to a heart by an electrode of an implantable medical device (IMD), a pace polarization artifact is generally created at the electrode-tissue interface. The pace polarization artifact is subsequently stored by the electrode. Such pace polarization artifact is generally minimized through the use of passive recharge circuitry. Such passive recharge circuitry functions in creating a recharge pulse at the electrode which in essence, minimizes the pace polarization artifact on the electrode. In order to produce further artifact minimization from a subsequent pacing pulse, following termination of the recharge pulse, the pace polarization artifact remaining on the electrode is sampled by the IMD, and this sample is analyzed by the IMD to determine whether it is at a desirable level. If not at such desirable level, software within the IMD is used to accordingly compensate the next recharge pulse in order to further minimize the pace polarization artifact generated by the corresponding next pacing pulse. This sampling and optional compensation is then repeated for subsequent pacing pulses so that corresponding pace polarization artifacts can be effectively analyzed and if necessary, minimized by corresponding subsequent recharge pulses that are compensated.

Certain embodiments of the invention provide a method of reducing polarization on an implanted electrode used for electrically stimulating cardiac tissue. The method comprises providing an implantable medical device used for electrically stimulating cardiac tissue via one or more electrodes and used for sensing cardiac signals emanating from the cardiac tissue via one or more sense amplifiers. An electrical stimulation pulse generated by the device is delivered to the cardiac tissue via one of the electrodes. An electrical recharge pulse generated by the device is delivered to the cardiac tissue via the one of the electrodes, the electrical recharge pulse minimizing polarization on the one of the electrodes resulting from the electrical stimulation pulse. The polarization on the one of the electrodes is sensed after delivery of the electrical recharge pulse. A determination is made as to whether the magnitude of the sensed polarization is within a predetermined desirable range. An adjustment amount for the electrical recharge pulse is calculated if the sensed polarization is not within the predetermined desirable range. The adjustment amount is based on the sensed polarization and calculated towards minimizing the sensed polarization. The electrical recharge pulse is adjusted by the calculated adjustment amount for a subsequent electrical recharge pulse to improve the minimization of the polarization resulting from a subsequent electrical stimulation pulse.

Additionally, certain embodiments of the invention provide an implantable medical device for electrically stimulating cardiac tissue. The implantable medical device comprises a lead, a pulse generator, a sensor, and a processor. The lead conducts electrical pulses to an electrode on the lead, and the electrode is adapted for electrical contact with cardiac tissue. The pulse generator is coupled to the lead to deliver electrical pulses to the cardiac tissue via the electrode, and the generator generates an electrical stimulation pulse and an electrical recharge pulse. The electrical recharge pulse minimizes polarization on the electrode resulting from the electrical stimulation pulse. The sensor senses the polarization on the one of the electrodes after delivery of the electrical recharge pulse. The processor calculates an adjustment amount for the electrical recharge pulse if the sensed polarization is not within a predetermined desirable range. The adjustment amount is based on the sensed polarization and calculated towards minimizing the sensed polarization, with the processor adjusting the electrical recharge pulse by the calculated adjustment amount for a subsequent electrical recharge pulse.

Further, certain embodiments of the invention provide a computer readable medium that provides instructions, which when executed on a processor, cause said processor to perform operations for reducing polarization on at least one electrode. The processor is within a controller of an implantable medical device for electrically stimulating cardiac tissue via the at least one electrode, wherein the implantable medical device is also used for sensing cardiac signals emanating from the cardiac tissue via at least one sense amplifier. The operations comprise creating an electrical stimulation pulse to stimulate cardiac tissue via one electrode; generating an electrical recharge pulse for delivery to the cardiac tissue via the one electrode to minimize polarization remaining on the one electrode from the electrical stimulation pulse; sampling the polarization remaining on the one electrode a certain time after the electrical recharge pulse is delivered; determining whether the sampled polarization is at a desirable level; calculating an adjustment amount for the electrical recharge pulse if the sampled polarization is not within the predetermined desirable range, where the adjustment amount is based on the sampled polarization and calculated towards minimizing the sensed polarization; and adjusting the electrical recharge pulse by the calculated adjustment amount for a subsequent electrical recharge pulse to improve the minimization of the polarization resulting from a subsequent electrical stimulation pulse.

DETAILED DESCRIPTION OF THE INVENTION

Figure 1:
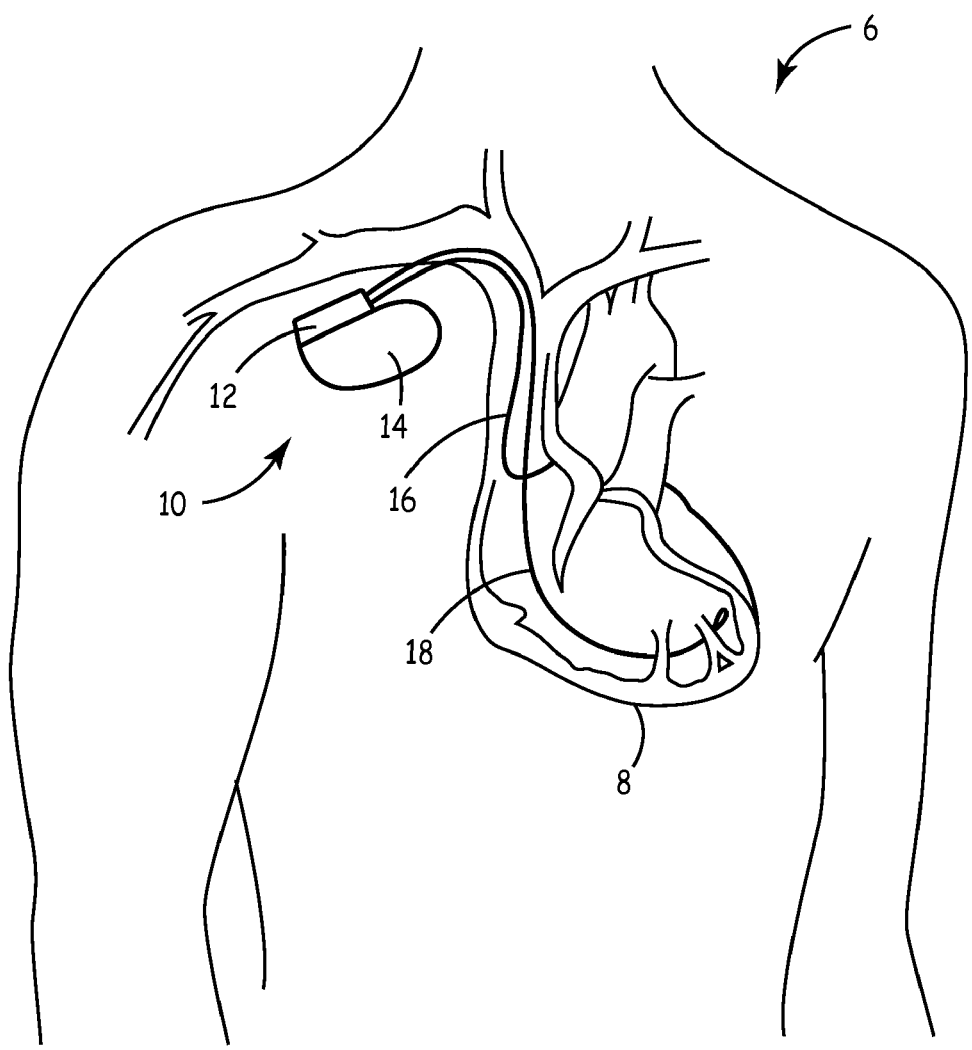
FIG. 1 illustrates an implantable medical device system in accordance with an embodiment of the invention implanted in a human body.

The following detailed description is to be read with reference to the drawings, in which like elements in different figures have like reference numerals. The drawings, which are not necessarily to scale, depict selected embodiments, but are not intended to limit the scope of the invention. It will be understood that many of the specific details of the vehicle incorporating the system illustrated in the drawings could be changed or modified by one of ordinary skill in the art without departing significantly from the spirit of the invention.

FIG. 1 is a simplified schematic view of one embodiment of implantable medical device ("IMD") 10 of the present invention implanted within a human body 6. IMD 10 comprises hermetically sealed enclosure 14 and connector module 12 for coupling IMD 10 to pacing and sensing leads 16 and 18 that are implanted near the proximal side in contact with the heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
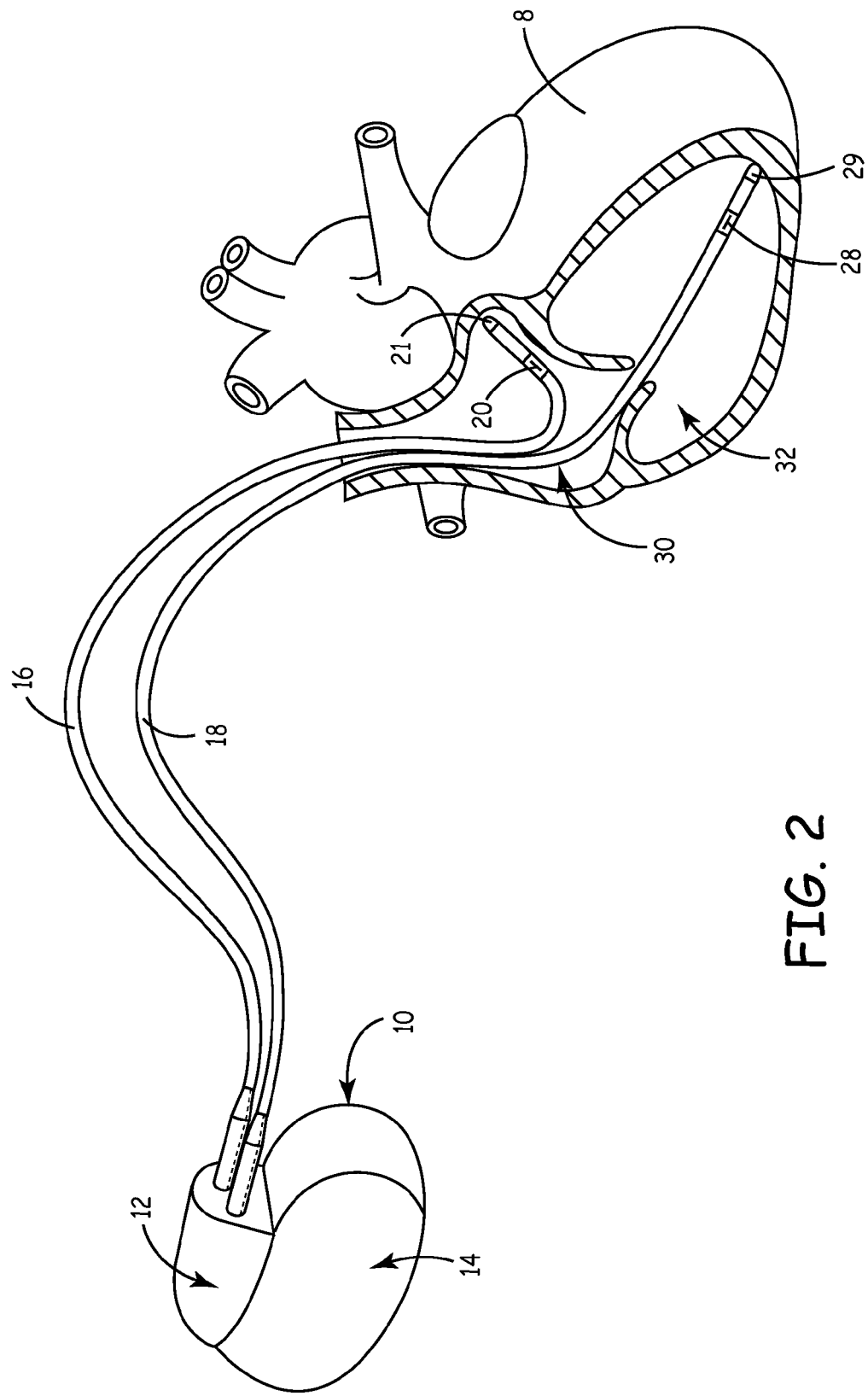
FIG. 2 illustrates one embodiment of an implantable pacemaker device system in accordance with the present invention coupled to a human heart.

FIG. 2 shows connector module 12 and hermetically sealed enclosure 14 of IMD 10 located in and near heart 8. Atrial and ventricular pacing leads 16 and 18 extend from connector module 12 to the right atrium 30 and ventricle 32, respectively, of heart 8. Atrial electrodes 20 and 21 disposed at the distal end of atrial pacing lead 16 are located in the right atrium 30. Ventricular electrodes 28 and 29 at the distal end of ventricular pacing lead 18 are located in the right ventricle 32.

Figure 3:
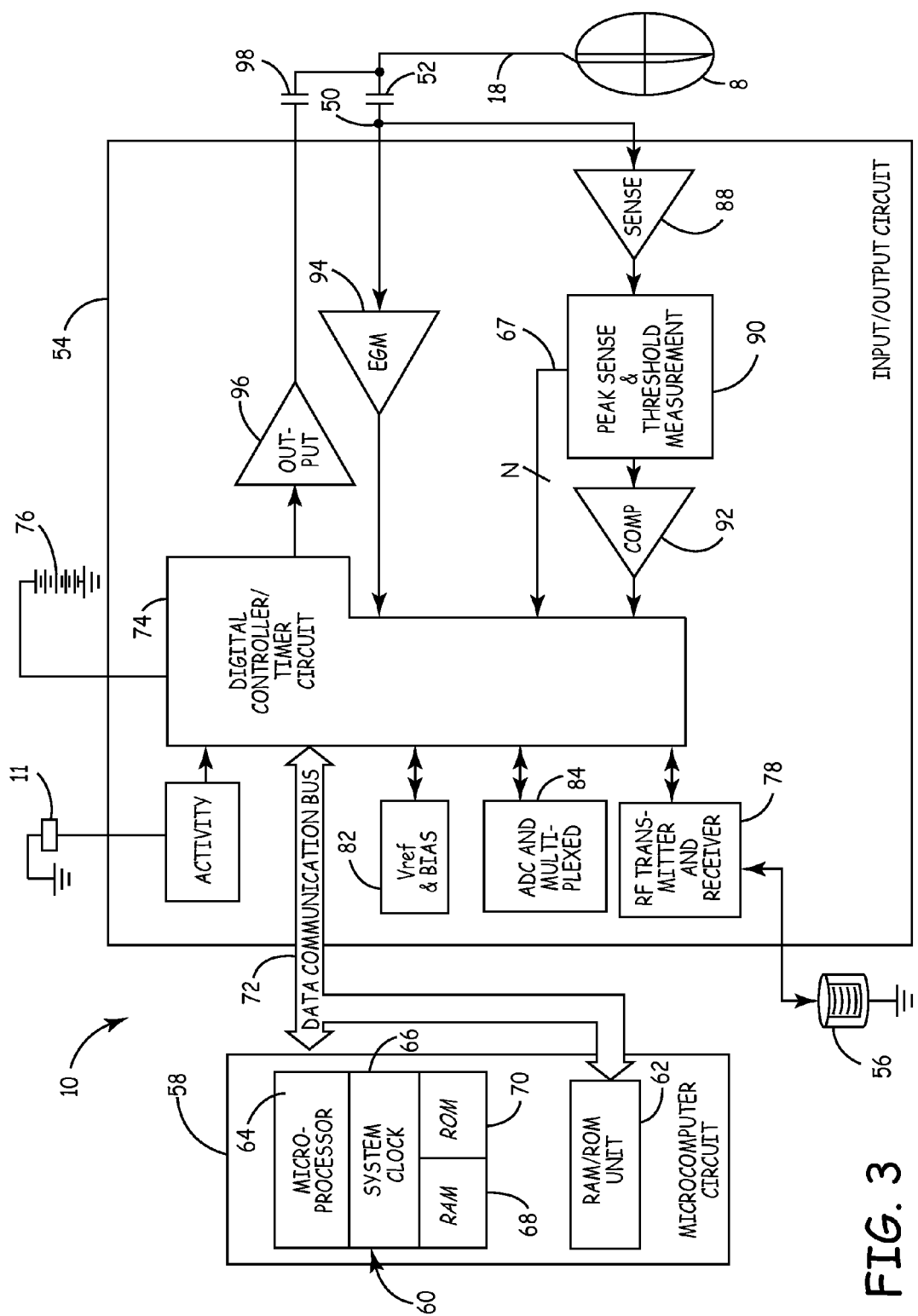
FIG. 3 is a block diagram illustrating the various components of one embodiment of an implantable pacemaker device configured to operate in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58, including rate response algorithms.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish an overall escape interval of the IMD 10 as well as various refractory, blanking and other timing windows for controlling the operation of peripheral components disposed within input/output circuit 54.

Digital controller/timer circuit 74 is preferably coupled to sensing circuitry 91, including sense amplifier 88, peak sense and threshold measurement unit 90 and comparator/threshold detector 92. Digital controller/timer circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8. Also, some embodiments of the invention can use active polarization compensation.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
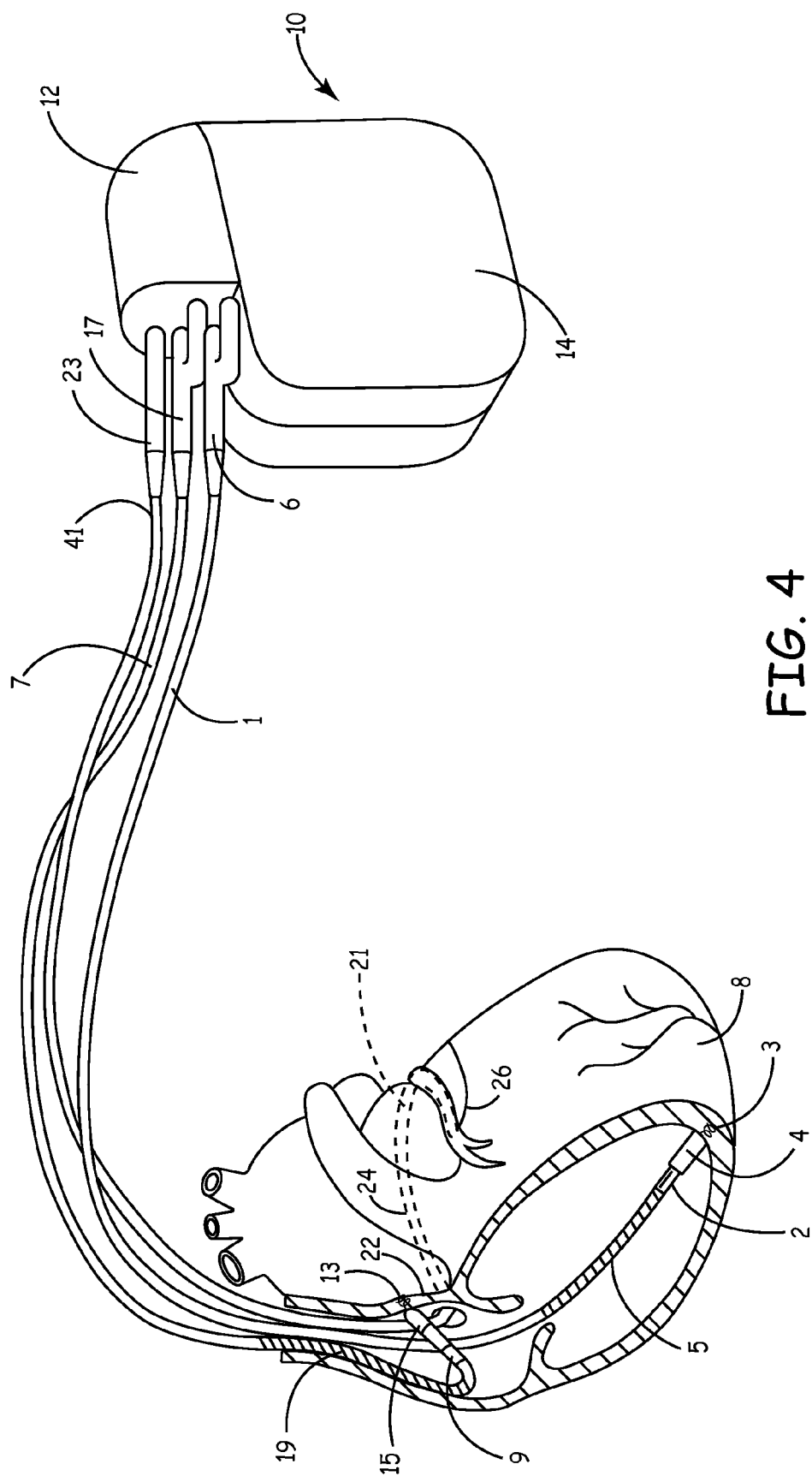
FIG. 4 illustrates one embodiment of an implantable pacemaker cardioverter defibrillator in accordance with the present invention coupled to a human heart.
Figure 5:
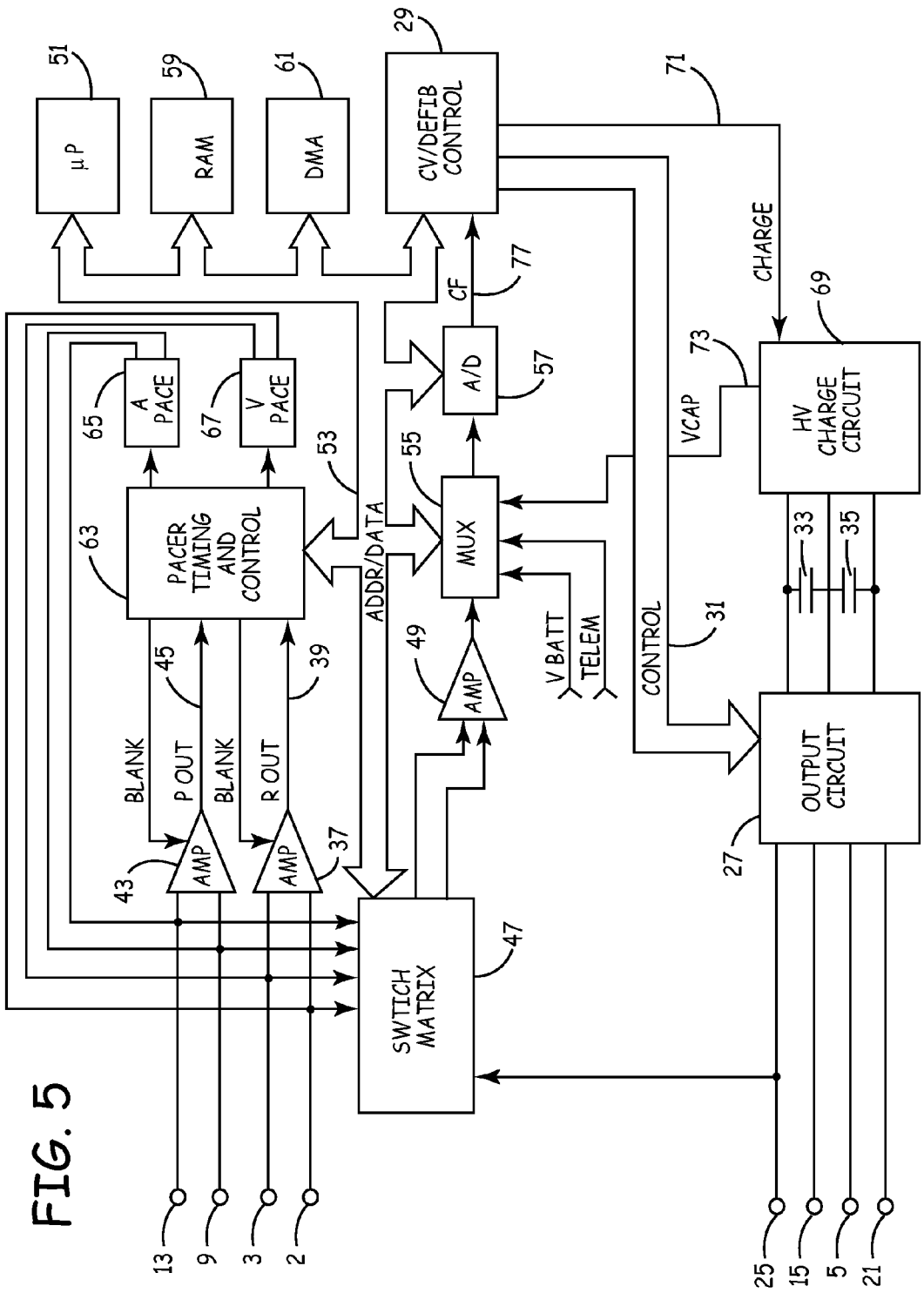
FIG. 5 is a block diagram illustrating the various components of one embodiment of an implantable pacemaker cardioverter defibrillator configured to operate in accordance with the present invention.

FIGS. 4 and 5 illustrate one embodiment of IMD 10 and a corresponding lead set of the present invention, where IMD 10 is a PCD. In FIG. 4, the ventricular lead can take the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference herein in its entirety.

Switch matrix 47 is used to select which of the available electrodes are coupled to wide band (0.5-200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular (AV) pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt-driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7-10, 1986, IEEE Computer Society Press, pages 167-170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541-547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses can be employed as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses can be employed such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry, which may be used to control delivery of monophasic pulses, is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

With various embodiments of medical devices, e.g., implantable medical devices, described above, it will become apparent from the description below that the present invention may be applied to any ventricular pacing system, e.g., dual chamber pacing system. For example, the present invention may be applied to a three-chamber atrial-bi-ventricular pacing apparatus, a dual chamber pacing apparatus, a dual chamber defibrillator, etc. In other words, for example, the present invention may be applied to any implantable medical device that provides bi-ventricular pacing. For example, some devices that may be modified to include the ventricular safety pacing techniques according to the present invention may include, for example, the InSync-ICD (e.g., Medtronic InSync ICD (Model 7272)), or InSync III three chamber atrial-bi-ventricular pacers; all VDD(R)/DDD(R) pacemakers including dual chamber right atrial/left ventricular pacers; Jewel DR DDD(R)-ICD; dual chamber (right atrial/left ventricular) defibrillators; three chamber DDD(R)-ICD pacing devices available from Medtronic Inc.; and other devices such as the Medtronic InSync Model 8040.

Figure 6:
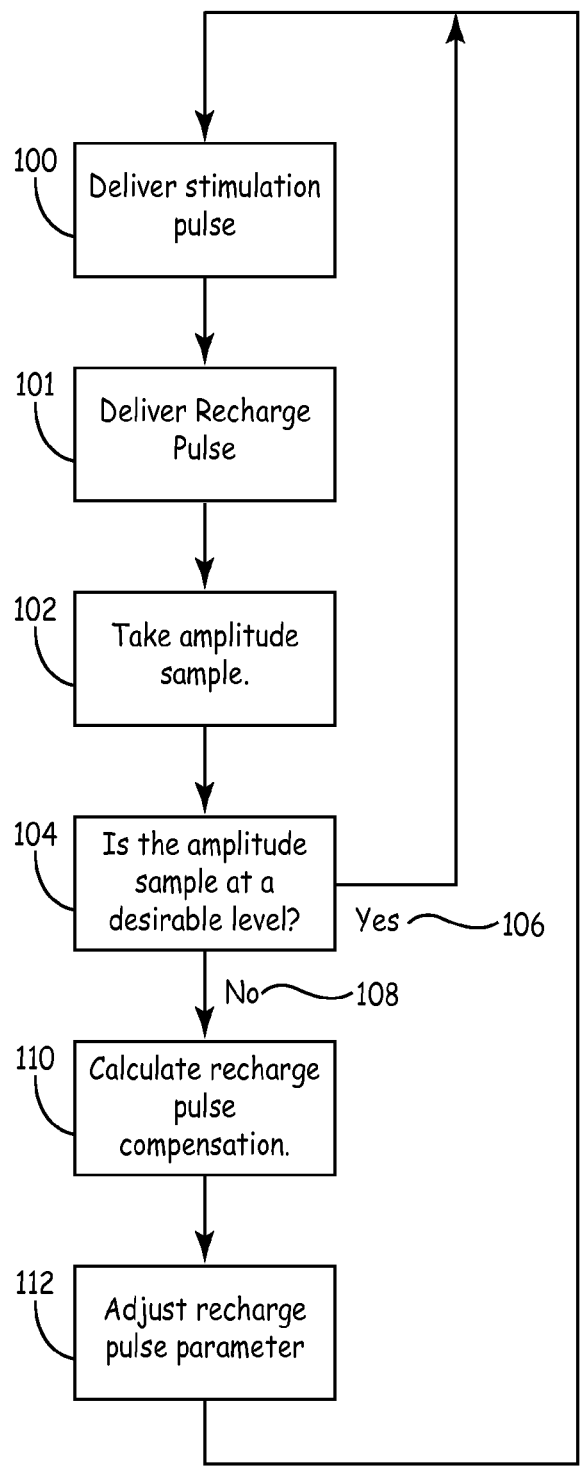
FIG. 6 is a flowchart illustrating one mode of operation of an implantable medical device operating according to the invention.

FIG. 6 is a flowchart illustrating one embodiment of the invention with IMD 10 providing cardiac therapy. In general, upon delivery of a pacing pulse to the heart 8 by an electrode of the IMD 10, a pace polarization artifact is typically created at the electrode-tissue interface. The pace polarization artifact is stored by the electrode. In several embodiments of the present invention, such pace polarization artifact is generally minimized through the use of recharge circuitry described below. Such recharge circuitry functions in creating a recharge pulse which in essence, minimizes the pace polarization artifact on the electrode. In order to produce further artifact minimization from a subsequent pacing pulse, following termination of the recharge pulse, the pace polarization artifact remaining on the electrode is sampled by the IMD 10, and this sample is analyzed by the IMD 10 to determine whether it is at a desirable level. If not at such desirable level, software within the IMD 10 is used to accordingly compensate the next recharge pulse in order to further minimize the pace polarization artifact generated by the corresponding subsequent pacing pulse. This sampling and optional compensation is then repeated for subsequent pacing pulses so that corresponding pace polarization artifacts can be effectively analyzed and if necessary, minimized by corresponding subsequent recharge pulses that are compensated.

It is to be appreciated that FIG. 6 references only one exemplary embodiment, and steps in the flowchart can be exchanged, modified, or even in some cases eliminated without diverting from the spirit of the invention. As described above, FIGS. 2 and 3 illustrate an embodiment of the invention for a pacemaker as the IMD 10, and FIGS. 4 and 5 illustrate an embodiment of the invention for a PCD as the IMD 10. Based on the system of the invention described below, the IMD 10 in each case would include a computer-based software product within a controller to facilitate the compensation with respect to the recharge pulse, if warranted. In addition, several aspects of the IMD 10 would have to be modified or adapted with respect to embodiments of the present invention. For example, the recharge circuitry would include dynamic components described below so that such circuitry can be adjusted in correspondence with the compensation of the recharge pulse. In addition, the standard blanking periods described below would be minimized in order to timely sample the pace polarization artifact as described. Further, a processor with memory described below would be used for programming at least one desirable level for polarization on the electrode, and such processor would be used to make determinations regarding whether compensation is necessary based on a comparison between the measured polarization sample and the stored desirable polarization level. As described below, such a desirable polarization level represents a level at which the polarization is not sufficient to mask the cardiac signals, which the pacemaker must detect. In certain embodiments, the processor is part of the controller including the computer-based software product. These and other modifications would generally be realized by those skilled in the art, and as such, need not an expansive discussion as it would also be generally known how to implement such modifications accordingly. Other than the computer-based software product and mentioned above, the functioning of the invention can generally be provided by using electrical components already included with the IMD 10 or by using electrical components that are generally known.

Figure 7:
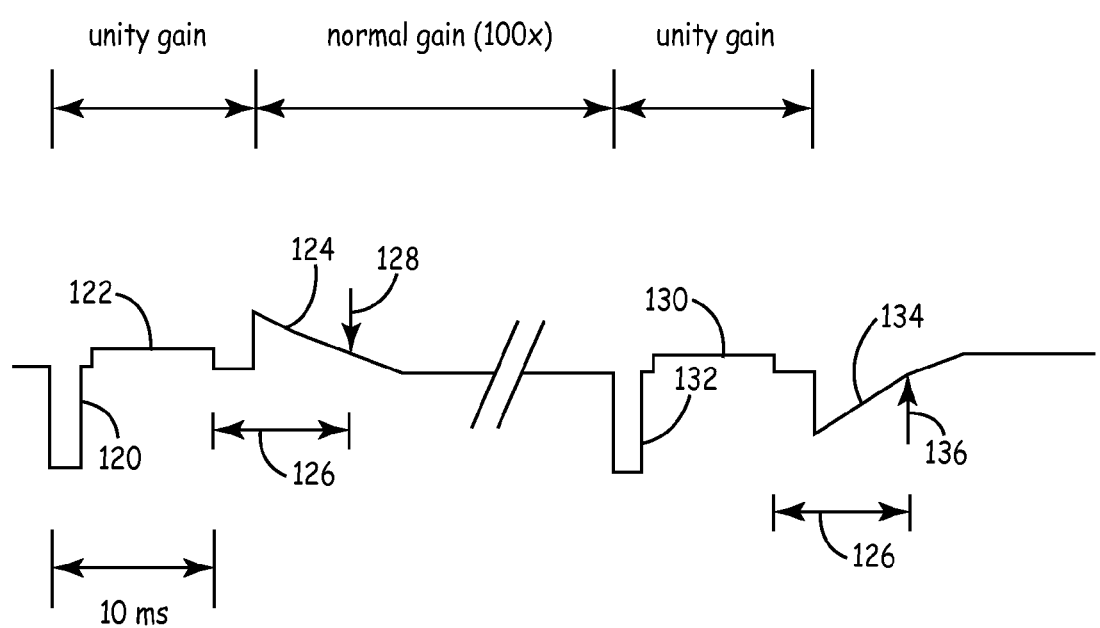
FIG. 7 is a timing diagram illustrating one electrical response of the heart when treated with an implantable medical device operating according to the one mode of operation of FIG. 6.

FIG. 7 is a timing diagram of electrical response of the heart during the flow chart steps illustrated in FIG. 6. An initial step 100 of the flowchart of FIG. 6 involves the IMD 10 delivering a stimulation pulse to the heart 8. This is illustrated with pulse 120 of FIG. 7. As mentioned herein, such pacing pulse 120 has an amplitude ranging in volts, e.g., from about 1 volt to about 10 volts, and is used to stimulate the heart at a region proximate to the electrode providing the pulse 120. Following delivery of such pulse 120, a recharge pulse 122 is provided, as described in step 101 of the flowchart of FIG. 6. The recharge pulse 122 is provided to minimize a pace polarization artifact 124 generally created by the pacing pulse 120 at the electrode-tissue interface. As described herein, the artifact 124 is stored on the stimulating electrode (e.g., tip electrode). Generally, the recharge pulse 122 has a lesser rise, but a longer run than that of the pacing pulse 120. The amplitude of the recharge pulse 122 is variable and, in certain embodiments, this amplitude is initially configured so that the area under the recharge pulse equals the area under the pacing pulse. It is to be appreciated that this mathematical balancing of the areas under the pacing and recharge pulses can be achieved via a microprocessor of the IMD 10. Alternatively, the recharge pulse 122 can be configured, by limiting the initial amplitude accordingly, to cause the area under the recharge pulse to be less than that of the area under the pacing pulse.

As shown in FIG. 7, in certain embodiments of the invention, after the pacing pulse 120 and recharge pulse 122 terminate, the sensed cardiac signal is amplified to a normal gain (100×) from unity gain. The pace polarization artifact 124 cannot be visibly observed as part of the signal under unity gain; however, if the signal is optionally amplified to such normal gain (100×), as is illustrated soon after the recharge pulse 122 terminates, the artifact 124 is easily identifiable, and in turn, detectable from the base line. This amplification can be optionally provided to ensure that the evoked response of the heart is within the limited dynamic sensing range of the sense amplifiers of the IMD 10. As such, with the amplification, the pace polarization artifact can be differentiated to a greater extent (e.g., from the base line) so as to provide a much more precise sampling of the artifact, and if warranted, a better correction for the subsequent recharge pulse in order to provide more of a minimizing effect on a subsequent artifact. As also shown, compensation to the recharge pulse may cause the pace polarization artifact to flip-flop on the baseline, where the artifact (following termination of the recharge pulse) is located either above the base line (e.g., artifact shown as 124) or below the base line (e.g., subsequent artifact shown as 134). Generally, when the software product is utilized to compensate a subsequent recharge pulse, if the software product initially overcompensates for the pace polarization artifact, then the subsequent artifact will be above the base line, and if the software product initially undercompensates for the artifact, than the subsequent artifact will be below the base line.

Following a predetermined delay 126 after termination of the recharge pulse 122, a sample amplitude 128 of the pace polarization artifact 124 remaining on the electrode is measured by the IMD 10, represented in step 102 of FIG. 6. Such sampling is conducted as soon as possible after termination of the recharge pulse 122 and restoration of normal gain. Such prompt sampling provides a significant sampling of the pace polarization artifact 124, and in turn, a good estimate for compensating a subsequent recharge pulse (if warranted), leading to reduction of a subsequent pace polarization artifact created by a subsequent pacing pulse. As shown, the sample amplitude 128 is taken after the predetermined delay 126. The sampling delay 126 is generally a characteristic of the electronics utilized, and such delay 126 is generally minimized when possible. One reason for minimizing the delay 126 lies in the nature of the cardiac condition that is being treated by the IMD 10. For example, for tachycardia or fibrillation conditions, in which the heart 8 is contracting at a very high rate, the type of therapy (anti-tachycardia and defibrillation respectively) required involves delivering a high rate of pacing pulses, e.g., with at least one pacing pulse for every contraction of the heart 8. For such cardiac conditions, the duration between each heart contraction is greatly reduced (e.g., the evoked response occurs roughly within about 5 to 20 milliseconds after the QRS wave) from what is normal (e.g., typically ranging in hundreds of milliseconds). As such, it is desirable to sample the polarization artifact 124 with as little delay as possible after the recharge pulse terminates so as to sample before a T-wave occurs. In so doing, a subsequent artifact can be minimized (if warranted) for corresponding subsequent pacing pulses in order for the sense amplifiers to be able to be differentiate the subsequent T-wave. If the sampling occurs after the T-wave, the artifact for the subsequent pacing pulse may be reduced, but may still hide the subsequent T-wave. In certain embodiments, the system is designed with a delay 126 of not greater than about 10 milliseconds after termination of the recharge pulse 122.

Once the sample 128 of the pace polarization artifact 124 is measured, a determination is made by the IMD 10 as to whether the sample amplitude is at a desirable level, as is referenced in step 104 of FIG. 6. Generally, designating this desirable level is largely dependent on the level of polarization being encountered by the system; the larger the polarization level that the system encounters, the lower the signal to noise level and the lower the dynamic ranger for the sensing amplifiers of the system, and the desirable level is accordingly designated. As mentioned previously, sense amplifiers of the IMD 10 typically sense in the millivolt range. In addition, the sense heart cardiac signals typically sensed by the sense amplifiers have amplitudes ranging in millivolts, e.g., from about 1 millivolt to about 10 millivolts. As such, in certain embodiments, the desirable level for the sample amplitude is set to be in the range between about +1 millivolt and about −1 millivolt; however, this can vary accordingly if polarization levels are higher than the norm (e.g., higher than 1 volt). As mentioned herein, such desirable level can be preprogrammed in memory of a processor in the IMD 10 and such processor can be used to make such determination regarding the sample amplitude. If the sample amplitude is determined to be at a desirable level as referenced by step 106 of FIG. 6, the process is looped back to step 100 with regard to generating another stimulation pulse without any compensation being calculated and provided for a subsequent recharge pulse. As such, the recharge pulse amplitude remains unchanged (i.e., with no compensation of such occurring), and will remain unchanged as long as the sample amplitude of the pace polarization artifact is further determined to be at a desirable level for subsequent cardiac cycles. As such, the flowchart will continue to loop back in this fashion so long as the sampled amplitudes of subsequent pace polarization artifacts remain at or below the desirable level.

If the sample amplitude is determined not to be at a desirable level as described above, as referenced by step 108, compensation for a subsequent recharge pulse amplitude is then calculated using the software product (e.g., programmed in a processor of the IMD 10) mentioned earlier, referenced in step 110 of FIG. 6. Such calculation generally involves using the following equation:

$$V_{Sx+1} = V_{Sx} * (1 - \alpha * V_{sample(x)}),$$ (I)

where $V_{Sx}$ is the amplitude of the recharge pulse for that cardiac cycle, $V_{sample(x)}$ is the measured sample amplitude of the pace polarization artifact for that cardiac cycle, $\alpha$ is a constant, and $V_{Sx+1}$ is the amplitude of the subsequent recharge pulse for the subsequent cardiac cycle. From such equation, one can see that if the measured sample amplitude $V_{sample(x)}$ is 0 (i.e., indicating a measurement at the base line with no pace polarization artifact), the subsequent recharge amplitude $V_{Sx+1}$ will equal the recharge pulse amplitude $V_{Sx}$, thus requiring no compensation of the subsequent recharge. This is the ideal case. However, in reference to the flowchart of FIG. 6, to have reached step 110, the sample amplitude is known to be at an undesirable level, and not 0. Thus, the measured sample amplitude $V_{sample(x)}$ is multiplied in the equation by a constant $\alpha$. Generally, the nature of the compensation lies heavily on the value assigned to constant $\alpha$. For example, if the constant $\alpha$ is made too small, the compensation to the subsequent recharge pulse is slight, and in turn, the impact on the subsequent pace polarization artifact is slight as well, in which case a number of subsequent recharge pulses would likely have to be additionally compensated before significant minimization of the artifact is achieved. Conversely, if the constant $\alpha$ is made too large, the compensation to the subsequent recharge pulse is large, and in turn, the impact on the subsequent pace polarization artifact is large as well so as to cause swings of the artifact on either side of the base line from cycle to cycle (causing the artifact to go from one polarity to the next from cycle to cycle, or beat to beat). Selecting a value for constant $\alpha$ is also based on pulse amplitude and duration, and design characteristics of the lead. Constant $\alpha$ is generally programmable and can be modified as desired. In certain embodiments, the constant $\alpha$ is equal to about 0.2, generally causing the compensation to the subsequent recharge pulse and impact on the subsequent pace polarization artifact to be slight.

The case described above with respect to having the constant $\alpha$ too large is generally shown in FIG. 7. Following calculation of the recharge pulse compensation in step 110 of FIG. 6, the calculated recharge pulse amplitude is subsequently applied to the subsequent recharge pulse 130, referenced as step 112. As described herein, the recharge pulses 122 and 130 of FIG. 7 are generally created via recharge circuitry of the IMD 10. In many IMDs, this recharge circuitry includes one or more capacitors as is generally known in the art. Examples of such systems are disclosed in U.S. Pat. Nos. 4,343,312 and 5,964,787, which are incorporated herein by reference. For example, the one or more capacitors can be placed in the circuit to create the recharge pulse of opposite polarity to minimize the pace polarization artifact. Alternatively or in combination, one or more resistors can be placed in the circuit to drain a portion of the pace polarization artifact from the electrode. In such embodiments, the circuitry may also include a transistor, where the transistor is actively turned off (e.g., to not affect the delivery of the pacing pulse) and on (e.g., to allow for a portion of the artifact to drain into the resistor). In certain embodiments of the invention, the recharge circuitry would have at least one active element having a characteristic, which could be altered. As such, by altering the characteristic, the functioning of the recharge circuitry could be changed so as to alter the recharge pulse in accordance with the compensation calculation. For example, with respect to the examples above, the active device could be a variable resistor being substituted for the resistor, whereby the resistance value of the variable resistor could be modified based on the compensation calculation for the recharge pulse. By changing this characteristic of one of the components of the recharge circuitry, the pace polarization artifact can be further minimized. In certain embodiments, the recharge circuitry includes an output amplifier used to control the generation of the recharge pulse. As such, the amplifier can be used to either affect voltage or current with respect to creation of the recharge pulse described below.

Following step 112, the flowchart of FIG. 6 loops back to step 100 involving the generation of a stimulation pulse. This is illustrated with pacing pulse 132 of FIG. 7. Following delivery of such pulse 132, the subsequent recharge pulse 130 is provided in step 101 via the recharge circuitry (as exemplified above) to minimize a corresponding pace polarization artifact 134 generally created by the pacing pulse 132 at the electrode-tissue interface. Subsequently, the other steps of the flowchart are encountered again where the amplitude of the artifact 134 is sampled at 136 as referenced in step 102 of FIG. 6 and a determination is made on whether the amplitude sample is at a desirable level in step 104 of FIG. 6 for the subsequent artifact 134 created.

Cardiac rhythm is generally analyzed before therapy is provided. As such, in certain embodiments, if the cardiac cycle of the heart is found to be of a long enough duration before therapy, certain embodiments of the invention can subsequently provide polarization compensation with multiple recharge pulses being generated per cardiac cycle. As such, the pace polarization artifacts can be minimized more quickly in comparison to the embodiment described herein involving one recharge pulse per cycle being generated per cycle. This technique is exemplified in FIGS. 8 and 9, and involves much of the invention process already thoroughly covered with respect to FIGS. 6 and 7. As such, there is less discussion with respect to FIGS. 8 and 9 in comparison.

Figure 8:
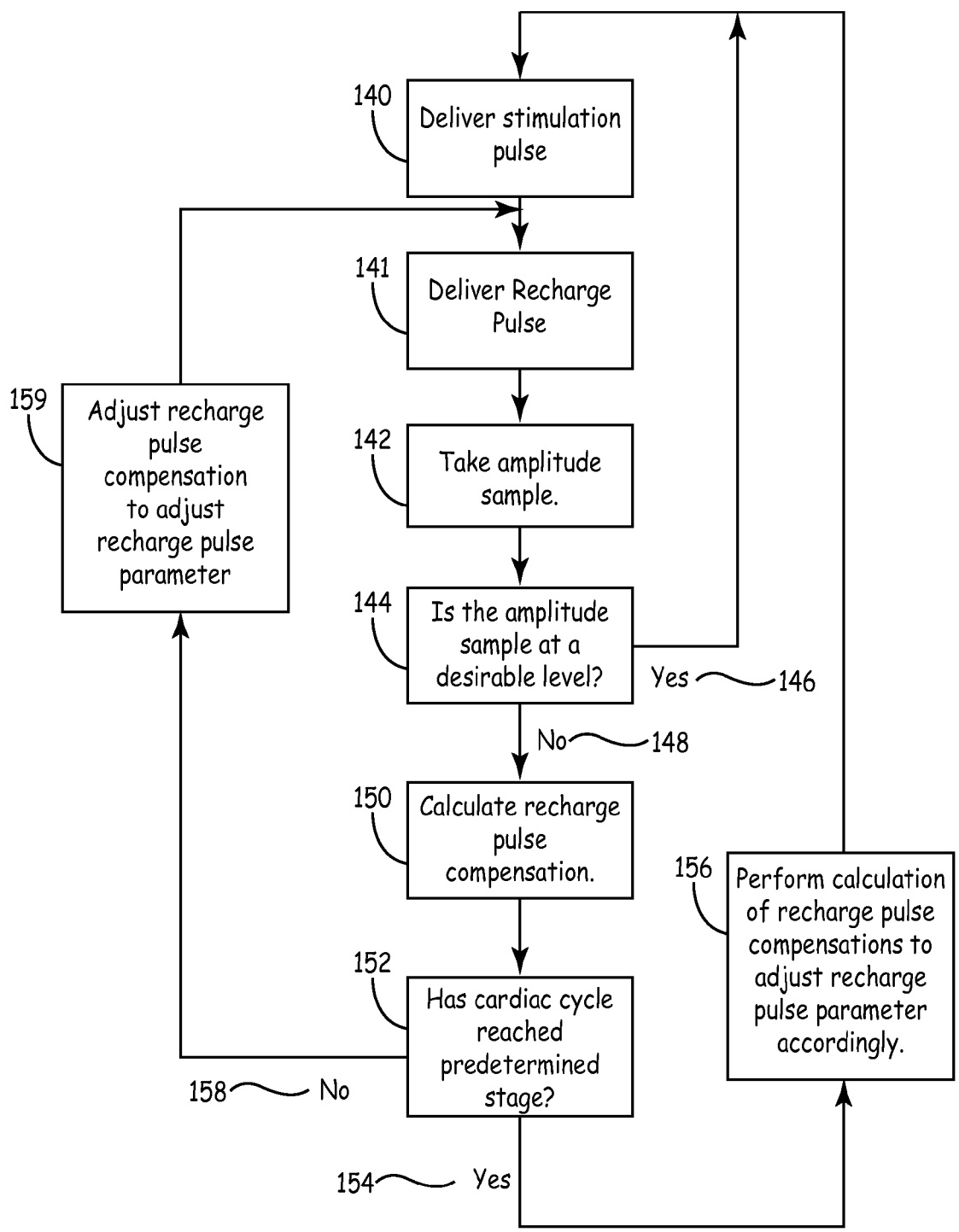
FIG. 8 is a flowchart illustrating a further mode of operation of an implantable medical device operating according to the invention.
Figure 9:
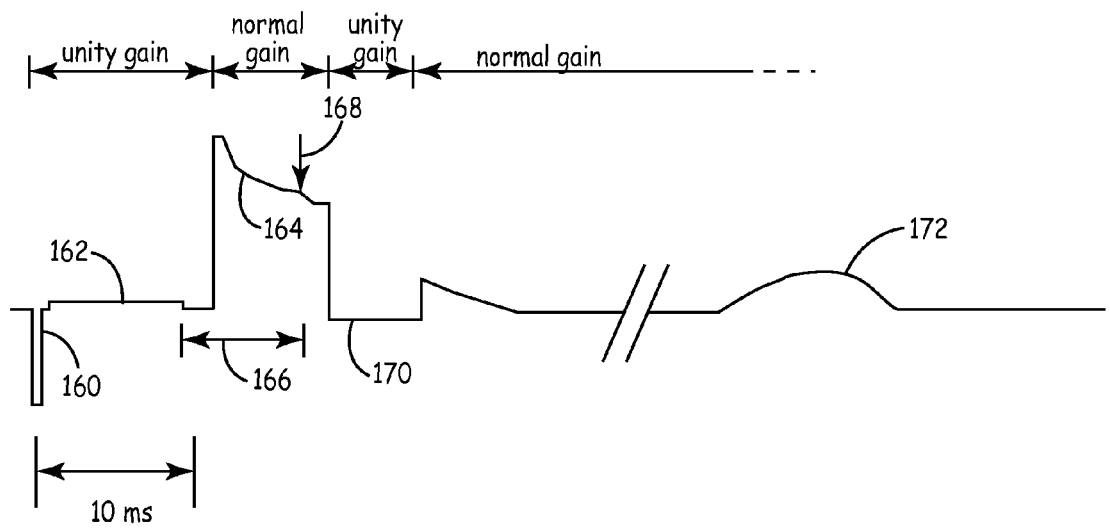
FIG. 9 is a timing diagram illustrating one electrical response of the heart when treated with an implantable medical device operating according to the further mode of operation of FIG. 7.

FIG. 8 is a flowchart illustrating one embodiment of the invention with the IMD 10 providing cardiac therapy, and FIG. 9 shows a timing diagram of electrical response of the heart during the flow chart steps illustrated in FIG. 8. An initial step 140 of the flowchart of FIG. 8 involves the IMD 10 delivering a stimulation pulse to the heart 8. This is illustrated with pulse 160 of FIG. 9. Following delivery of such pulse 160, an initial recharge pulse 162 is provided via recharge circuitry in step 141 of the flowchart of FIG. 8 to minimize a pace polarization artifact 164 generally created by the pacing pulse 160 at the electrode-tissue interface. As shown in FIG. 9, in certain embodiments of the invention, after the pacing pulse 160 and recharge pulse 162 terminate, the sensed cardiac signal is amplified to a normal gain (100×) from unity gain. Following a delay 166 after termination of the recharge pulse 162, an amplitude sample 168 of the pace polarization artifact 164 remaining on the electrode is measured by the IMD 10, represented in step 142 of FIG. 8.

Once the sample amplitude 168 of the pace polarization artifact 164 is measured, a determination is made by the IMD 10 as to whether the sample amplitude is at a desirable level, as is referenced in step 144 of FIG. 8. As mentioned previously, in certain embodiments, the desirable level for the sample amplitude is in the range of between about +1 millivolt and about −1 millivolt. Such desirable level can be pre-programmed in memory of a processor in the IMD 10 and such processor can be used to make such determination regarding the sample amplitude. If the sample amplitude is determined to be at a desirable level as referenced by step 146 of FIG. 8, the process is looped back to step 140 with regard to generating another stimulation pulse without any compensation being calculated and provided for a subsequent recharge pulse. As such, the flowchart will continue to loop back in this fashion so long as the sampled amplitudes of subsequent pace polarization artifacts remain at or below the desirable level. If the sample amplitude is determined not to be at a desirable level as described above, as referenced by step 148, compensation for a subsequent recharge pulse amplitude is calculated in step 150 of FIG. 8, using the software product mentioned above. Such calculation generally involves using Equation I discussed above. Following calculation of the recharge pulse compensation in step 150 of FIG. 8, the calculated recharge pulse amplitude is subsequently adjusted for a subsequent recharge pulse, referenced as step 156 or step 159.

As shown in FIG. 9 and described above, the system can be designed so that the subsequent recharge pulse occurs during the same cardiac cycle as the initial recharge pulse 162, almost immediately after the sample amplitude 168 is taken. However, it is desirable for the recharge pulses to occur at least a certain time duration before a T-wave (shown as 172) occurs in order to not interfere with the detection of the T-wave in the cardiac cycle. As such, after the recharge pulse compensation is calculated in step 150, a determination is made in step 152 of FIG. 8 as to whether the cardiac cycle has reached a predetermined stage. Such predetermined stage is generally a designated point in time during the cardiac cycle, and is measured from any of a number of reference events. In certain embodiments, the reference event is the stimulation pulse 160 and the predetermined stage is the point in time following such reference event, e.g., after 100 milliseconds. If the predetermined stage has been reached as referenced by step 154 of FIG. 8, the process is looped back to step 140 with respect to generating another stimulation pulse. As such, the process will involve going through the subsequent steps accordingly. However, before the stimulation step 140, in certain embodiments, as described in step 156, the system performs a calculation involving the recharge pulse compensations calculated during this previous cardiac cycle and adjusts the recharge pulse parameter based on this calculation. In certain embodiments, this calculation can involve averaging recharge sample amplitudes calculated during this previous cardiac cycle; however, the invention should not be limited as such as the calculation can involve any averaging or any other computation as desired. The recharge pulse parameter calculated in step 156 is then used in providing the initial recharge pulse that follows the upcoming stimulation pulse. Step 156 is used to provide an adequate amplitude for the initial recharge pulse of the following cardiac cycle. If the predetermined stage has not been reached as referenced by step 158 of FIG. 8, the process is looped back to step 141 where a subsequent recharge pulse 170 is delivered followed by another amplitude sample being taken (generally after a time delay) in step 142, in which the sample is taken this time for the subsequent recharge pulse 170. As such, the process will involve going through the subsequent steps accordingly. However, before being looped back to step 141 in this fashion, the recharge pulse compensation calculated in step 150 is modified in step 159 to adjust the recharge pulse parameter. This modification is performed so that the polarization on the electrode is generally not overcompensated. In certain embodiments, the recharge pulse compensation is reduced by half in step 159 before being used in delivering the recharge pulse in step 141; however, the invention should not be limited as such as the adjustment made can be modified as desired.

As shown in FIG. 9, the subsequent recharge pulse 170 is again represented in the timing diagram under normal gain (100×). However, it should be appreciated that by applying such subsequent recharge pulse 170 during the same cardiac cycle, overcompensation may occur with respect to minimizing the pace polarization artifact in this fashion. In certain embodiments, this overcompensation can be counteracted by decreasing the duration of the subsequent recharge pulse 170. In other certain embodiments, the calculated recharge pulse amplitude can be varied so as to not potentially cause overcompensation. For example, the calculated recharge pulse amplitude could be reduced (e.g., by half) before being used in providing the subsequent recharge pulse.

Figure 10:
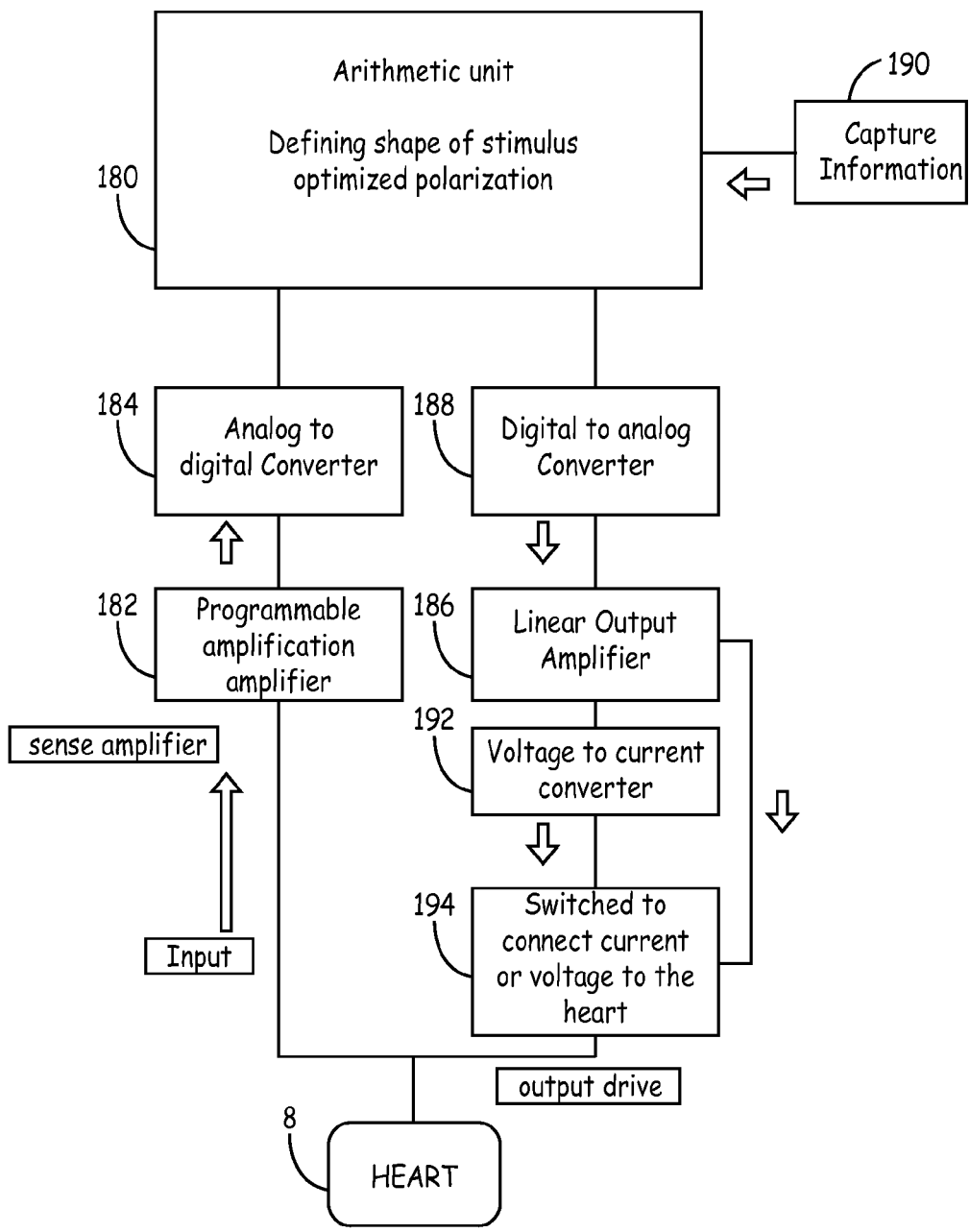
FIG. 10 is a block diagram showing the system schematic of one embodiment of the invention.

FIG. 10 is a block diagram illustrating one embodiment of the invention that can be used with IMD 10 of FIG. 3 or 5. As previously mentioned, certain embodiments of the invention include a computer-based software product (arithmetic unit) 180. Such product 180 would be electrically linked to amplifiers 182, 186, which in turn would be electrically linked to the heart 8. The amplifier 182 includes one or more sense amplifiers, and can be represented by amplifier 94 in FIG. 3 and by amplifiers 37, 43 in FIG. 5. The amplifier 182 is used to sense the evoked response of the heart 8, similar to the functioning of amplifiers 94 in FIG. 3 and amplifiers 37, 43 in FIG. 5. However, the sense amplifier 182 also includes a programmable function, by which the sensed cardiac response may be amplified as desired. In certain embodiments, as shown in FIGS. 7 and 9, the amplification is programmed to occur following certain events in the evoked response (e.g., following termination of the recharge pulses 122, 130, 162, and 170) and to last for certain durations (e.g., lasting until a subsequent pacing pulse 132 or recharge pulse 170 occurs). As shown in FIG. 10, the sense amplifier 182 is used with an analog-to-digital (A-to-D) converter 184. Such converter 184 is not separately shown in FIGS. 3 and 5; however, amplifier 94 of FIG. 3 is shown feeding into a digital controller/timer circuit 74. Similarly, FIG. 5 shows a pacer timing and control 63. As such, one function of amplifier 94 and/or pacer timing and control 63 can be to digitally convert the input analog signal. It is generally desirable to digitize the incoming signal in order to provide better analysis of the sensed signal. In addition, a resulting digitized signal is much easier to store and recreate if digitized.

The manipulated evoked response signal is subsequently sent to the computer-based software product 180. Such computer software product 180 can be represented by microcomputer circuit 58 in FIG. 3 and by microprocessor 51 and RAM 59 in FIG. 5. While it is not specifically represented, signal transmission from and to the computer software product 180 will generally occur over a data communications bus represented by 72 in FIG. 3 and by 53 in FIG. 5. As shown, in certain embodiments, transmission between the amplifiers 182 and 186 (of FIG. 10) and the data communications bus (not shown) occurs via converters 184 and 188, respectively. Capture information 190 represents the sampled amplitude (of the pace polarization artifact) referenced by 128 or 136 in FIG. 7 and by 168 in FIG. 9. Such capture information 190 can be collected by one or more sense amplifiers (not shown) and subsequently transferred to the computer-based software product 180 by the data communications bus (not shown).

As discussed herein, the software product 180 is used to calculate the recharge pulse amplitude compensation, if warranted. Following such calculation, the compensation signal is output to amplifier 186. As such, in certain embodiments, the software product 180 will use both a buffer (not shown) to store digital pulse samples of the recharge pulse, and a timing circuit (not shown) to output the samples as designed to generate the waveform pulse. The amplifier 186 includes one or more output amplifiers, and can be represented by amplifier 96 in FIG. 3 or by amplifiers 65, 67 in FIG. 5. In being output to the amplifier 186, the signal is initially converted back to analog form using digital-to-analog (D-to-A) converter 188. As mentioned above, in certain embodiments, the output amplifier 186 is generally included with the recharge circuitry so as to control the generation of the recharge pulse. As such, the amplifier 186 can be used to either affect voltage or current (by using a voltage-to-current converter 192) with respect to the recharge pulse generation. Whether voltage or current is designated for the system, one or more switches 194 ultimately control when the output pulse (whether recharge or pacing pulse) is delivered. In certain embodiments, the switches 194 can be coupled to the heart 8 via one or more capacitors. For further protective purposes, the switches 194 can be normally open, except during delivery of the output pulses. Also, in certain embodiments, the switches 194 can be tied to a timing circuit (not shown) so as to selectively control when the output waveform is delivered to the heart 8. The switches 194 can additionally be controlled, in certain embodiments, so as to dictate which part of the heart 8 receives the output waveform, e.g., via atria or ventricle leads.

In using the system shown in FIG. 10, one is able to digitally sample both the input and output waveform signals to the software product 180. As such, the signals are recognized as sample quantities having certain polarity, amplitude, and duration. For example, when the pacing pulses 120 and 132 of FIG. 7 and 160 of FIG. 9 are sensed, they will be recognized as a quantity of negative samples having certain amplitude and duration. Conversely, when the recharge pulses 122 and 130 of FIG. 7 and 162 and 170 of FIG. 9 are sensed, they will be recognized as a quantity of positive samples (or negative with respect to 170 of FIG. 9) having certain amplitude and duration. As mentioned previously, when the system initially starts sensing, in certain embodiments, these pacing and recharge pulse samples may be mathematically balanced; however, after such initial sensing and following compensation by the system, a ratio of the samples will start being established between the pacing and recharge pulse samples so that the recharge pulse can be varied to minimize the pace polarization artifact on the electrode. For example, in the initial sensing stage, the system may recognize two negative samples for a pacing pulse (having certain amplitude and duration), which may mathematically balance with four positive samples for a recharge pulse (having certain amplitude and duration). This mathematical balance is such that the area under the pacing pulse is equal to the area under the recharge pulse in an analog setting. Following this, the system may compensate the recharge pulse in a subsequent cycle. As previously described herein, this involves the amplitude of the subsequent recharge pulse being modified, e.g., decreased or increased, to more adequately minimize the pace polarization artifact on the electrode. As such, the amplitude would be modified so that it is created using different variations with respect to sample quantity or size. For example, if the recharge pulse is reduced in size (e.g., recharge pulse amplitude is decreased), then the number or size of samples may in turn be reduced to create the compensated recharge pulse amplitude. As such, one is able to more accurately control the shape of the recharge pulse samples to produce the warranted recharge pulse with mathematical balancing. With respect to creating recharge pulse samples using either voltage or current signals as a basis, it should be appreciated that more exact ratios between the pacing and recharge pulse samples can be achieved in using current signals as charge on the electrode is easier to quantify.

It is to be appreciated that with the compensation of the recharge pulses, the invention should not be limited with respect to simply adjusting the amplitude of the recharge pulse. For example, the duration of the recharge pulse could be adjusted to subsequently minimize the pace polarization artifact. It is to be realized that this could be done instead of or in combination with the amplitude, as desired. While exemplary embodiments have been described, it should be understood that various changes, adaptations, and modifications may be made therein without departing from the spirit of the invention and the scope of the appended claims.

What is claimed is:

1. An implantable medical device for electrically stimulating cardiac tissue, comprising:
   a) a lead that conducts electrical pulses to an electrode on the lead, the electrode adapted for electrical contact with cardiac tissue;
   b) a pulse generator coupled to the lead and configured to deliver electrical pulses to the cardiac tissue via the electrode, the generator generating an electrical stimulation pulse and an electrical recharge pulse, the electrical recharge pulse for minimizing polarization on the electrode resulting from the electrical stimulation pulse;
   c) a sensor configured to sense the polarization on the one of the electrodes, the sensor sensing the polarization after delivery of the electrical recharge pulse; and
   d) a processor configured to calculate an adjustment amount for the electrical recharge pulse if the sensed polarization is not within a predetermined desirable range, the adjustment amount being based on the sensed polarization and calculated towards minimizing the sensed polarization, the processor adjusting the electrical recharge pulse by the calculated adjustment amount for a subsequent electrical recharge pulse.

2. The implantable medical device of claim 1, wherein the implantable medical device is a pacemaker.

3. The implantable medical device of claim 1, wherein the electrodes on the cardiac tissue are located for providing anti-tachycardia therapy.

4. The implantable medical device of claim 1, wherein the processor is a digital signal processor.

\* \* \* \* \*